(12) United States Patent
Therkelsen et al.

(10) Patent No.: US 9,382,205 B2
(45) Date of Patent: Jul. 5, 2016

(54) PROCESSES FOR THE MANUFACTURE OF A PHARMACEUTICALLY ACTIVE AGENT

(71) Applicant: H. Lundbeck A/S, Valby (DK)

(72) Inventors: Frans Therkelsen, Holbrek (DK); Michael Harold Rock, Frederiksberg C (DK); Svend Treppendahl, Virum (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/553,029

(22) Filed: Nov. 25, 2014

(65) Prior Publication Data

US 2015/0080584 A1    Mar. 19, 2015

Related U.S. Application Data

(63) Continuation of application No. 13/875,623, filed on May 2, 2013, now Pat. No. 8,901,318, which is a continuation of application No. 12/972,559, filed on Dec. 20, 2010, now Pat. No. 8,461,353.

(60) Provisional application No. 61/289,530, filed on Dec. 23, 2009.

(51) Int. Cl.
*C07D 209/14* (2006.01)
*C07D 209/16* (2006.01)

(52) U.S. Cl.
CPC ............ *C07D 209/16* (2013.01); *C07D 209/14* (2013.01)

(58) Field of Classification Search
CPC .................................................. C07D 209/14
USPC ........................................................ 548/504
See application file for complete search history.

(56) References Cited

U.S. PATENT DOCUMENTS

| | | | |
|---|---|---|---|
| 3,042,685 | A | 7/1962 | Allais et al. |
| 7,157,488 | B2 | 1/2007 | Chen et al. |
| 8,044,090 | B2 * | 10/2011 | Chen et al. ............... 514/418 |
| 8,461,353 | B2 | 6/2013 | Therkelsen et al. |
| 8,901,318 | B2 | 12/2014 | Therkelsen et al. |
| 2009/0163545 | A1 | 6/2009 | Goldfarb |

FOREIGN PATENT DOCUMENTS

| | | |
|---|---|---|
| CN | 101531624 | 9/2009 |
| EG | 2005020066 | 2/2005 |
| GB | 846675 | 8/1960 |
| IL | 166815 | 4/2010 |
| WO | WO 02/078693 | 10/2002 |
| WO | WO 2007/070796 | 6/2007 |
| WO | WO 2009/037308 | 3/2009 |
| WO | WO 2010/036362 | 4/2010 |

OTHER PUBLICATIONS

International Search Report for PCT/DK2010/050348, mailed Jun. 15, 2011.
Office Action in Egyptian Application No. 2012061152, issued Apr. 3, 2014, 5 pages.
Bergmann et al., "5- and 6-ftuoro-3-indoleacetic acid," Journal of the Chemical Society, p. 1913-1914, 1959.
Bergmann et al., "6-ftuoro-6-methoxy-, and 7-methoxylryptophan," Journal of the Chemical Society, p. 2827-2829, 1962.
Buzas et al., "Synthesis and reactions of 1-acetyl-2-benzylidene-3-oxo-2,3-dihydroindoles," Synthesis, 6, p. 458-461, 1989.
Diker et al., "Trapping if iminiums by the indole nucleus during catalytic hydrogenation of the nitriles: a rapid synthesis of tetrahydro-beta-carbolines," Tetrahedron Letters, 36(14):2497-2500, 1995.
Freifelder, "A low pressure process for the reduction of nitriles. Use of Rhodium catalyst," Journal of the American Chemical Society, 82, p. 2386-2389, 1960.
Grandberg et al., "Indoles. XXXVI. Method for the synthesis of 2-unsubstituted tryptamines," Chemistry of Heterocyclic Compounds, 9(2):196-201, 1973.
Jahangir et al., "A new route to the indolepyridonaphthyridine ring system: synthesis of N-benzyl-13b.14-dihydronauclefine and N-benzyl-13b.14-dihydroangustine." Tetrahedron. 43(24):5761-5768, 1987.
Yang et al., "Synthesis of DL-6-ftuorotryptophan," Shengwu Huaxue Yu Shengwu Wuli Jinzhan-Biochemistry and Biophysics, 41:66-69, 1981.
Comprehensive utilization of diethoxymethane for producing ethyl formate and paraformaldehyde, Xikang et al., China Academic Journal Electronic Publishing House, p. 46, 1982 and English translation, 2 pages.
"The Fifth Series of Experimental Chemistry", Murata, The Chemical Society of Japan, 2007, Fifth edition, vol. 14, pp. 352-356 and English translation, 12 pages.

\* cited by examiner

*Primary Examiner* — Shawquia Jackson
(74) *Attorney, Agent, or Firm* — Wilmer Cutler Pickering Hale and Dorr

(57) ABSTRACT

Disclosed herein are processes for the preparation of a pharmaceutically active agent and pharmaceutically acceptable salts thereof.

19 Claims, No Drawings

PROCESSES FOR THE MANUFACTURE OF A PHARMACEUTICALLY ACTIVE AGENT

This application is a continuation of U.S. application Ser. No. 13/875,623, filed May 2, 2013, which is a divisional of U.S. application Ser. No. 12/972,559, filed Dec. 20, 2010, now U.S. Pat. No. 8,461,353, issued on Jun. 11, 2013, which claims priority from U.S. Provisional Application Ser. No. 61/289,530, filed Dec. 23, 2009, the contents of which are incorporated by reference herein.

FIELD OF THE INVENTION

The present invention relates to the preparation of N-[2-(6-fluoro-1H-indol-3-yl)ethyl]-3-(2,2,3,3-tetrafluoropropoxy) benzylamine and pharmaceutically acceptable salts thereof.

BACKGROUND ART

The 5-$HT_6$ receptor is a member of the G-protein coupled receptor superfamily of serotonin receptors, and, like the 5-$HT_4$ and 5-$HT_5$ receptors, is positively coupled to adenylate cyclase (Monsma, F. et al. *Mol. Pharmacol.* 1993, 43, 3, 320-327). The rat 5-$HT_6$ receptor was first cloned in 1993 and the cloning of the human homologue, to which it shares an 89% sequence identity, was reported in 1996 (Kohen, R. et al. *J Neurochem.* 1996, 66, 1, 47-56). The localization of 5-$HT_6$ receptors in rat brain has been studied using mRNA quantification by Northern analysis and RT-PCR, immunohistochemistry, and autoradiography (Ward, R., et al. *J. Comp Neurol.* 1996, 370, 3, 405-414; and Ward, R. et al. Neuroscience 1995, 64, 4, 1105-1111). These methods have consistently found high levels of the receptor in olfactory tubercle, hippocampus, striatum, nucleus accumbens, and cortical regions. 5-$HT_6$ receptors are either absent or present in very low levels in peripheral tissues.

Much of the early interest in the 5-$HT_6$ receptor was due to the observation that several psychotropic agents are high affinity antagonists at the human 5-$HT_6$ receptor. These compounds include amitriptyline (Ki=65 nM) and the atypical antipsychotics clozapine (Ki=9.5 nM), olanzapine (Ki=10 nM), and quetiapine (33 nM). See Roth, B. L., et al. *J. Pharmacol. Exp. Ther.* 1994, 268, 3, 1403-1410.

The use of selective 5-$HT_6$ receptor antagonists to treat cognitive dysfunction is widely accepted and is based on several lines of reasoning. For example, selective 5-$HT_6$ receptor antagonists modulate cholinergic and glutamatergic neuronal function. Cholinergic and glutamatergic neuronal systems play important roles in cognitive function. Cholinergic neuronal pathways are known to be important to memory formation and consolidation. Centrally acting anti-cholinergic agents impair cognitive function in animal and clinical studies and loss of cholinergic neurons is one of the hallmarks of Alzheimer's disease. Conversely, stimulation of cholinergic function has been known to improve cognitive performance and two agents currently approved for the treatment of cognitive deficit in Alzheimer's disease, galantamine and donepezil, are both acetylcholinesterase inhibitors. The glutamatergic system in the prefrontal cortex is also known to be involved in cognitive function (Dudkin, K. N., et al. *Neurosci. Behav. Physiol.* 1996, 26, 6, 545-551).

The activity of selective 5-$HT_6$ receptor antagonists is also demonstrated in animal models of cognitive function. Since the disclosure of the first selective 5-$HT_6$ receptor antagonists, there have been several reports on the activity of these selective compounds in models of cognitive function. For example, the selective 5-$HT_6$ receptor antagonist SB-271046 improved performance in the Morris water maze (Rogers, D. et al. *Br. J. Pharamcol.* 1999, 127 (suppl.): 22P). These results were consistent with the finding that chronic i.c.v. administration of anti-sense oligonucleotides directed toward the 5-$HT_6$ receptor sequence led to improvements in some measures of performance in the Morris water maze (Bentley, J. et al. *Br. J. Pharmacol.* 1999, 126, 7, 1537-42). SB-271046 treatment also led to improvements in the spatial alternation operant behavior test in aged rats.

Currently, several 5-$HT_6$ receptor antagonists are in clinical development as potential treatments for cognitive dysfunction disorders. A first report that a 5-$HT_6$ receptor antagonist, SB-742457, is of clinical benefit in Alzheimer's patients provides further evidence of the therapeutic potential of this approach.

N-[2-(6-fluoro-1H-indol-3-yl)ethyl]-3-(2,2,3,3-tetrafluoropropoxy)benzylamine is a potent and selective 5-$HT_6$ receptor antagonist which is currently in clinical development. Its chemical structure is depicted below as the compound of Formula I.

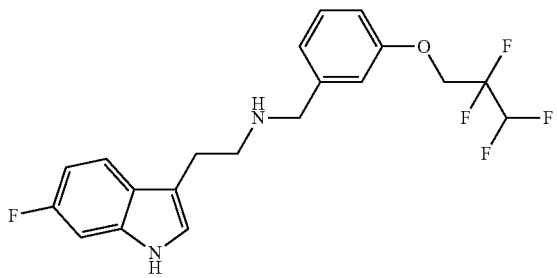

Formula I

The synthesis of N-[2-(6-fluoro-1H-indol-3-yl)ethyl]-3-(2,2,3,3-tetrafluoropropoxy)benzylamine, its use for the treatment of disorders such as cognitive dysfunction disorders, and pharmaceutical compositions comprising this substance are disclosed in U.S. Pat. No. 7,157,488 ("the '488 patent"). The '488 patent further describes the preparation of the corresponding monohydrochloride salt.

Although the synthetic methods disclosed in the above-identified reference suffices to prepare small quantities of material, it suffers from a variety of safety issues, low yields or processes that are not amendable to large scale synthesis. Thus, an unmet need exists to identify processes for the manufacture of the compound of Formula I.

Accordingly, the present invention describes an efficient and economical process for the preparation of the compound of Formula I that is useful for the production of kilogram quantities of material for preclinical, clinical and commercial use. In particular, the inventors have unexpectedly discovered the role of ammonia to prevent dimerization in connection with the reduction of the nitrile containing intermediate to the corresponding amine.

SUMMARY OF THE INVENTION

The present invention relates to a process for the preparation of N-[2-(6-fluoro-1H-indol-3-yl)ethyl]-3-(2,2,3,3-tetrafluoropropoxy)benzylamine, and pharmaceutically acceptable salts thereof, comprising the steps of:
(a) reacting 6-Fluoroindole with an iminium ion species generated in-situ from formaldehyde and dimethylamine in the presence of an acidic aqueous solution to produce the compound of Formula II

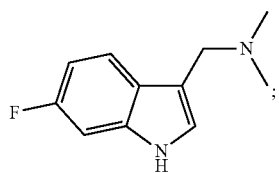

Formula II (b) reacting the compound of Formula II with KCN in the presence of DMF/water to produce the compound of Formula III;

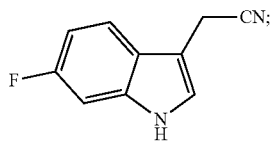

Formula III (c) hydrogenating the compound of Formula III with $H_2$ in the presence of $NH_3$ using a transition metal catalyst to produce the compound of Formula IV;

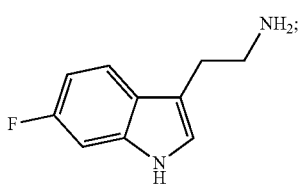

Formula IV and
(d) reacting the compound of Formula IV with 3-(2,2,3,3-tetrafluoropropoxy)benzaldehyde in the presence of a solvent followed by the addition of reducing agent.

A separate aspect relates to a process for the preparation of the compound of formula II comprising the steps of:

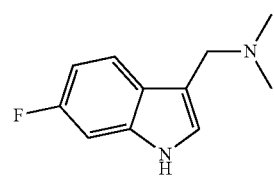

Formula II (a) mixing a solution of diethoxymethane, water and formic acid;
(b) adding the solution of step (a) to a mixture of 6-fluoroindole, methylamine and acetic acid; and
(c) adding an aqueous basic solution.

In one embodiment, the solution of step (a) is mixed at a temperature from about 75° C. to about 85° C.

In another embodiment, the solution of step (a) is stirred for less than about 2 hours.

In yet another embodiment, the solution of step (a) is added to a mixture of 6-fluoroindole and acetic acid at a temperature from about 2-8° C.

In another embodiment, the aqueous basic solution is NaOHaq.

In one embodiment, the yield is greater than 90%. In one embodiment, the yield is greater than 95%. In a separate embodiment, the yield is greater than 98%.

Another aspect relates to a process for the preparation of the compound of formula IV comprising the steps of:

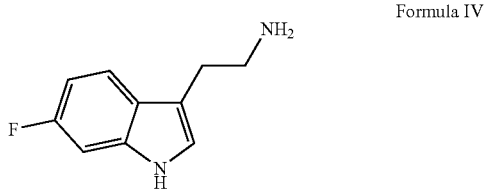 [SMILES: NCCc1c[nH]c2cc(F)ccc12]

Formula IV (a) mixing (6-fluoro-1H-indol-3-yl)acetonitrile, 25% $NH_3$ in water and a transition metal catalyst in an alcoholic solvent; and
(b) hydrogenating the mixture with $H_2$.

In one embodiment, the transition metal catalyst is RaNi.

In another embodiment, the alcoholic solvent is methanol.

In yet another embodiment, the hydrogenation is run at a pressure of about 2.5 bars for about 16 hours.

In one embodiment, the hydrogenation is run at a temperature from about 55° C. to about 65° C.

Yet another aspect of the invention relates to a process for the purification of 2-(6-fluoro-1H-indol-3-yl)-ethylamine comprising the steps of:

(a) dissolving 2-(6-Fluoro-1H-indol-3-yl)-ethylamine in an alcoholic solvent;
(b) adding a solution of L(+)-tartaric acid; and
(c) capturing the tartaric acid salt as a precipitate.

In one embodiment, the alcoholic solvent is methanol.

In one embodiment, ethyl acetate is used with the alcoholic solvent.

DETAILED DESCRIPTION

As previously indicated, the present invention is based on the discovery of a feasible process that can obtain N-[2-(6-fluoro-1H-indol-3-yl)ethyl]-3-(2,2,3,3-tetrafluoropropoxy)benzylamine, and pharmaceutically acceptable salts thereof, in an efficient and economical manner. The invention is explained in greater detail below but this description is not intended to be a detailed catalog of all the different ways in which the invention may be implemented, or all the features that may be added to the instant invention.

Accordingly, the invention was achieved by the development of the novel process described in Scheme I.

Scheme I

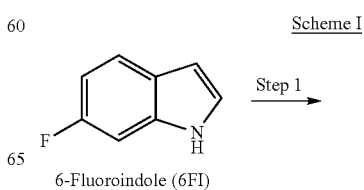

6-Fluoroindole (6FI)

Step 1

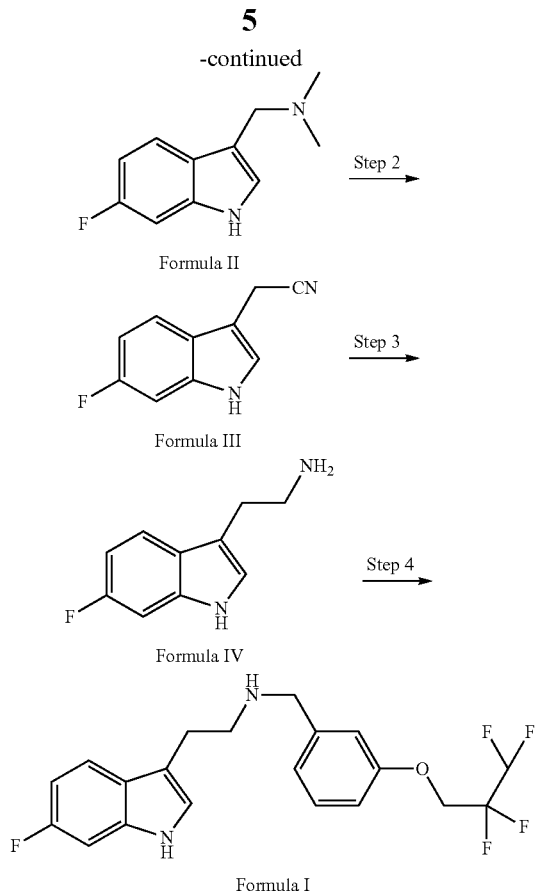

Formula II

Formula III

Formula IV

Formula I

The process starting from commercially available 6-Fluoroindole can be characterized as follows:

In the first step, commercially available 6-fluoroindole is converted to (6-fluoro-1H-indol-3-ylmethyl)-dimethylamine. This transformation involves a mannich reaction which generates an iminium ion species in-situ. In one embodiment, the iminium ion species is generated in-situ from diethoxymethane and dimethylamine. In another embodiment, the iminium ion species is generated in-situ from formaldehyde and dimethylamine. In another embodiment, the reaction is run in an aqueous solvent.

In the second step, (6-fluoro-1H-indol-3-ylmethyl)-dimethylamine is converted to (6-fluoro-1H-indol-3-yl)acetonitrile by reaction with potassium cyanide in the presence of DMF/water at elevated temperature. In another embodiment, the elevated temperature is about the reflux temperature of the reaction mixture.

In the third step, (6-fluoro-1H-indol-3-yl)acetonitrile is converted to 2-(6-fluoro-1H-indol-3-yl)-ethylamine. This transformation involves the reduction of the nitrile to the primary amine using hydrogen and a transition metal catalyst the presence of ammonia. In another embodiment, the transition metal catalyst is Raney Ni.

In the fourth step, 2-(6-Fluoro-1H-indol-3-yl)-ethylamine is converted to N-[2-(6-fluoro-1H-indol-3-yl)ethyl]-3-(2,2,3,3-tetrafluoropropoxy)benzylamine by coupling the amine with 3-(2,2,3,3-tetrafluoropropoxy)benzaldehyde in the presence of a solvent followed by the reduction of the imine bond with a reducing agent. This transformation is a reductive amination reaction. In one embodiment, the reducing agent is sodium borohydride.

A considerable advantage of the process according to the invention consists in the fact that the use of ammonia in the third step unexpectedly prevents the undesired dimerization of (6-fluoro-1H-indol-3-yl)acetonitrile while allowing the reaction to proceed smoothly and in high yield. Although the hydrogenation of basic nitriles with Raney Nickel has been known for some time (Huber, W. *JACS* 1944, 66, 876-879), the use of only Raney Nickel in the preparation of the compound of formula I may not be practical.

The use of ammonia as a reaction additive to work in concert with catalyst promoters such as Raney Nickel (Robinson and Snyder, Organic Syntheses Collective Volume 3, 720-722) has been disclosed. However, the prior art points to the fact that the use of ammonia appears to decrease overall activity (Thomas-Pryor, et al. *Chem. Ind.* 1998, 17, 195; Viullemin, et al. *Chem. Eng. Sci.* 1994, 49, 4839-4849; and Fouilloux, New Frontiers in Catalysis—Proceedings of the 10th International Congress on Catalysis, 1992, Elsevier Science, Amsterdam, 255-2558). For additional examples, see EP 0913388, WO 00/27526, WO 99/22561, U.S. Pat. No. 5,777,166, and U.S. Pat. No. 5,801,286. Thus, the prior art appears not to teach nor suggest the use of ammonia in the reduction of nitriles with Raney Nickel due to the decreased overall activity that is observed.

To this end, the inventors have unexpectedly discovered that the use of ammonia in this process allows the reaction to proceed without decreasing overall activity while preventing the formation of undesired dimerization.

The following are definitions for various abbreviations as used herein:
"DEM" is Diethoxymethane.
"DMF" is N,N-Dimethylformamide.
"MeOH" is Methanol.
"THF" is Tetrahydrofuran.
"6Fl" is 6-Fluoroindole.
"RaNi" is an activated Nickel Catalyst which is optionally doped with Fe and Cr and that comes in different particle sizes. In one embodiment, the RaNi used is a sponge type metal catalyst commercially available from Fluka. In another embodiment, the RaNi used is Johnson Matthey A5009 (5%, 33 microns) catalyst. In yet another embodiment, the RaNi used is Degussa's B111 W catalyst.
"Cyanide source" is KCN, NaCN, and other agents which release the CN⁻ anion.
"Aq" is Aqueous.
"DI" is Distilled or Ultra Pure
"RT" is Room Temperature.
"eq" is Equivalence
"g" is Grams.
"ml" is Milliliter
"L" is Liter.
"kg" is Kilogram
"M" is Molar.
"w/w" is Weight per Weight
"HPLC" is High Performance Liquid Chromatography The compound of Formula I forms pharmaceutically acceptable acid addition salts with a wide variety of organic and inorganic acids and include the physiologically acceptable salts which are often used in pharmaceutical chemistry. Such salts are also part of this invention. Such salts include the pharmaceutically acceptable salts listed in Journal of Pharmaceutical Science, 66, 2-19 (1977) which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, a-hydroxybutyrate, butyne-1,4-dicarboxylate, hexyne-1,4-dicarboxylate, caprate, caprylate, cinnamate, citrate, formate, fumarate, glycollate, heptarioate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

EXPERIMENTAL SECTION

HPLC Description

The HPLC analysis was made under the following chromatographic conditions; column: Xterra RP18 (100 mm×4.6 mm, 3.5 μm), mobile phase: 10 mM Ammonium carbonate (pH 8.5)/Acetonitrile, 86/14 to 14/86 (v/v, %), flow rate: 2 ml/min, column temperature: about 45° C., detection: UV at 280 nm.

Example 1

Synthesis of the Compound of Formula II

Detailed syntheses of the compound of Formula II from commercially available 6-fluoroindole are provided-below. Scheme II uses diethoxymethane and dimethylamine to generate the "iminium ion species". An alternative procedure using formaldehyde in place of diethoxymethane is also provided below.

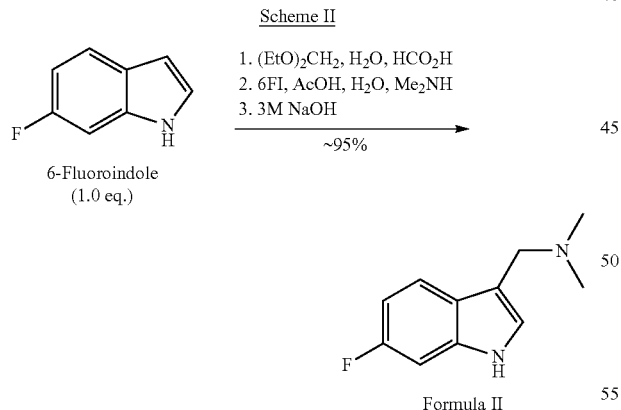

Synthetic Procedure:
Preparation of Formaldehyde was Carried Out in Reactor A. The Synthesis of the Compound of Formula 11 was Carried Out in Reactor B. Precipitation of the Final Product was Carried Out in Reactor C.

Procedure:
To reactor A were charged diethoxymethane (65 ml/54 g), water (50 ml) and formic acid (39 ml/47 g). The mixture was heated to about 80° C./reflux for about 2 hours and then cooled to about 20° C. To reactor B were charged 6-fluoroindole (50 g) and 80% acetic acid (66 ml/70 g, 2.5 eq. to 6-fluoroindole). The suspension was cooled to 2-5° C. 40% Dimethylamine (aq) (103 ml/92 g, 2.2 eq. to 6-fluoroindole) was added drop-wise to reactor B keeping the temperature below about 15° C. The reaction mixture was stirred for about 20 minutes and at the same time the temperature was adjusted to 2-4° C.

The mixture from reactor A (DEM, water, formic acid, formaldehyde and ethanol at about 20° C.) was added drop-wise to reactor B while keeping the temperature at 2-8° C. The reaction mixture was stirred for additional 10 minutes at 2-8° C. The reaction mixture was slowly warmed to about 40° C. over a 1 hour period. The reaction mixture was stirred at about 40° C. for an additional 1 hour. The reaction mixture was cooled to about 20° C.

To reactor C was charged 3M NaOH (800 ml, 1.24 eq. to the acetic acid+the formic acid) and the solution was cooled to about 10° C. The reaction mixture from reactor B was added drop-wise to the NaOH solution in reactor C while keeping the temperature at 10-15° C. (pH>14). The suspension was stirred for 40 minutes at 5-20° C. (pH>14). The product was collected by filtration and the filter-cake was washed twice with water (2×250 ml). The product was dried at about 60° C. under vacuum for 16 hours. Yield: 95%. Purity by HPLC (280 nm): 98 area %.

Procedure Using Formaldehyde in Place of Diethoxymethane:

To a 250 L reactor, under $N_2$ atmosphere, was charged with about 40% aqueous dimethylamine (35.68 kg, 1.0 eqv.) at about 17° C. The mixture was cooled to about 4.5° C. and glacial acetic acid (43.4 kg, 2.5 eq.) was added dropwise over 140 min while maintaining the temperature using below about 15° C. After stirring for 20 min at about 3° C., 37% aqueous formaldehyde (25.9 kg, 1.1 eq.) was slowly added over about 20 min while keeping the temperature between about 0° C. to about 10° C. 6-Fluoroindole (39.2 kg) was added. The reaction was exothermic and reached a final temperature of about 40° C., which was then cooled down to about 20° C. The reaction solution was slowly added in a 650 L reactor charged with aqueous 3M NaOH over a period of about 40 min. The suspension was stirred for about 40 min while keeping the temperature between about 5 and 20° C. The product was filtered, rinsed with DI water (120 kg) and dried at about 50° C. to afford the compound of Formula II (45.4 kg). Yield: 85%.

Example 2

Synthesis of the Compound of Formula III

A detailed synthesis of the compound of Formula III from the compound of Formula II is provided below in Scheme III.

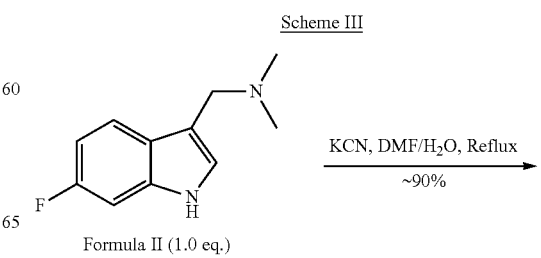

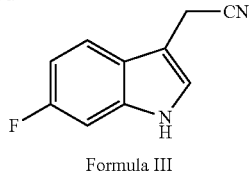

Formula III

Step-Wise Procedure:

(6-Fluoro-1H-indol-3-ylmethyl)-dimethylamine (65 g), KCN (31 g), DMF (195 ml) and water (104 ml) were charged to the reactor. The reaction mixture was heated to about 100-105° C. (strong reflux) for about 5-8 hours. The reaction mixture was cooled to 20-25° C. Water (780 ml) and toluene (435 ml) were charged to the reactor and the mixture was stirred vigorously for >2 hours. The organic and aqueous layers were separated. The organic layer was washed with 5% NaHCO$_3$ (6×260 ml), 2M HCl (260 ml), 5% NaHCO$_3$ (260 ml) and 5% NaCl (260 ml), respectively. The organic layer was filtered and concentrated to dryness. MeOH (260 ml) was added and the solution was concentrated to dryness. The compound of Formula III was isolated as a brown oil. Yield: 90%. Purity by HPLC (280 nm): 95%. MS m/z: 193 (M+H)$^+$.

Example 3

Synthesis of the Compound of Formula IV

A detailed synthesis of the compound of Formula IV is provided below in Scheme IV.

Scheme IV

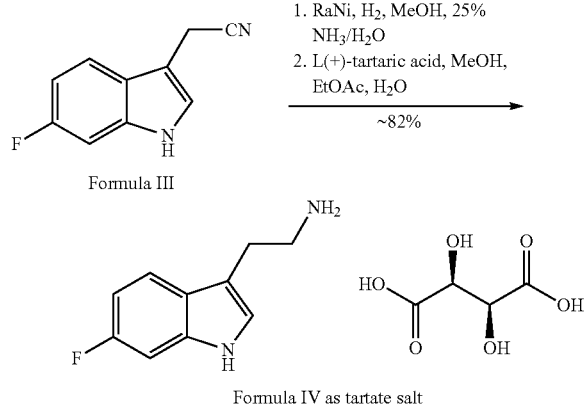

Formula III

1. RaNi, H$_2$, MeOH, 25% NH$_3$/H$_2$O
2. L(+)-tartaric acid, MeOH, EtOAc, H$_2$O

~82%

Formula IV as tartate salt

Synthetic Procedure:

The Reduction of the Compound of Formula III to Formula IV with Hydrogen was Performed in an Autoclave. Reactors a and Reactor B were Used to Prepare the RaNi Suspension and the Reagent Solutions which were Transferred to the Autoclave. Reactors C and D were Used During Work Up and Reactors E and F for the Isolation of the Compound of Formula IV as the Tartrate Salt.

Procedure:

To reactor A were charged RaNi (66 g, water-wet) and MeOH (600 ml). 25% NH$_3$ in H$_2$O (375 ml) was charged (by vacuum line) to the autoclave. The suspension of RaNi in MeOH from reactor A was transferred (by vacuum line) to the autoclave. 25% NH$_3$ in H$_2$O (200 ml) was charged to reactor A and then transferred (by vacuum line) to the autoclave. The compound of Formula III (211 g) and MeOH (500 ml) are charged to reactor B and then transferred (by vacuum line) to the autoclave. MeOH (600 ml) was charged to reactor B and then transferred (by vacuum line) to the autoclave. 25% NH$_3$ in H$_2$O (175 ml) was charged to reactor B and then transferred (by vacuum line) to the autoclave. The reaction mixture was ventilated with nitrogen (3×N$_2$ at about P 2-3 bars). The reaction mixture was ventilated with hydrogen (4×H$_2$ at P 2 bar). The hydrogen pressure was adjusted to about P 2 bar. The reaction mixture was heated to 60° C. The hydrogen pressure was adjusted to about P 2.5 bars. After about 16 hours at about 60° C. and P(H$_2$) 2.5 bars the reaction mixture is cooled to room temperature. The reaction mixture was ventilated with nitrogen (3×N$_2$ at P 2.0-3.0 bar).

The reaction mixture was transferred from the autoclave to reactor C. The autoclave was washed with MeOH (500 ml). The methanol was transferred to reactor C. The mixture was left without stirring for 2-16 hours. The supernatant was collected in reactor D. MeOH (350 ml) was charged to reactor D. The mixture was stirred slowly for 5 minutes and then left without stirring for 2-16 hours. The supernatant was collected in reactor D. The RaNi remains were collected for waste after destruction. Under a nitrogen atmosphere the supernatant in reactor D was filtered through celite. Additional MeOH (350 ml) was filtered through the celite to give a combined filtrate.

The filtrate was transferred to reactor E and concentrated under reduced pressure to approximately 2 volumes (~400-450 ml). MeOH (600 ml) was charged. The mixture was concentrated under reduced pressure to approximately 2 volumes (~400-450 ml). MeOH (600 ml) is charged. The mixture is concentrated under reduced pressure to approximately 2 volumes (~400-450 ml). MeOH (600 ml) was charged. The mixture was concentrated under reduced pressure to approximately 2 volumes (~400-450 ml). MeOH (1420 ml), ethyl acetate (1135 ml) and water (190 ml) were charged. The solution in reactor E was heated to reflux.

In reactor F were charged L(+) tartaric acid (163.6 g) and MeOH (1135 ml). The solution from reactor F was transferred to the solution in reactor E over 5-10 minutes, which results in precipitation of the desired product as the tartrate salt. The mixture was stirred for about 15 minutes at reflux and then cooled over 1 hour at 5-10° C. The mixture was stirred for about 1 hour at 5-10° C. The product was collected by filtration. The filter-cake was washed with cold ethyl acetate:MeOH (1:2, 380:760 ml). The white product was dried under vacuum at about 40-45° C. for 16 hours. Yield: 82%. Purity by HPLC (280 nm): 99-100 area %. MS m/z: 179 (M+H)$^+$.

Procedure Using BH$_3$-THF:

Alternatively, a BH$_3$-THF complex in place of the hydrogenation was also explored to reduce the nitrile of the compound of Formula III to the corresponding amine. A 1600 L reactor, under N$_2$ atmosphere, was charged at RT with a toluenic solution containing the compound of Formula III (18.46 kg). A 1M solution of borane-THF complex (211 kg, 2.2 eqv.) was slowly added to this solution over about 133 minutes while keeping the temperature between 15 and 25° C. The resulting yellowish solution was heated to about 65° C. and stirred at this temperature for about 1 hour. After cooling down to about 21° C., the reaction mixture was added dropwise over about 80 minutes to a well-stirred a 15% NaOH aqueous solution under N$_2$ flow. The biphasic mixture was slowly heated to about 50° C., stirred between about 50-60° C., heated to about 65° C. and stirred at this temperature for 1 hour.

After cooling down to about 25° C., the alkaline aqueous layer was decanted off for waste. The reaction mixture was then heated to about 50° C. in order to distill the THF under reduced pressure (about 0.2 barG). Dichloromethane (93 L) was added to the remaining aqueous phase and aqueous HCl (18.8 kg aqueous HCl 37% and 22 kg DI water) was slowly added over about 30 minutes at about 22° C. The reaction mixture was then left to stir at RT for about 2 hours before being filtered, washed twice with dichloromethane (2×19 L) and dried overnight under reduced pressure to afford the compound of Formula IV as the monohydrochloride salt. Yield: 72% as 17.3 kg.

Example 4

Synthesis of the Compound of Formula I

The detailed synthesis of N-[2-(6-fluoro-1H-indol-3-yl) ethyl]-3-(2,2,3,3-tetrafluoropropoxy)benzylamine as the monohydrochloride salt is provided in Scheme V.

Scheme V

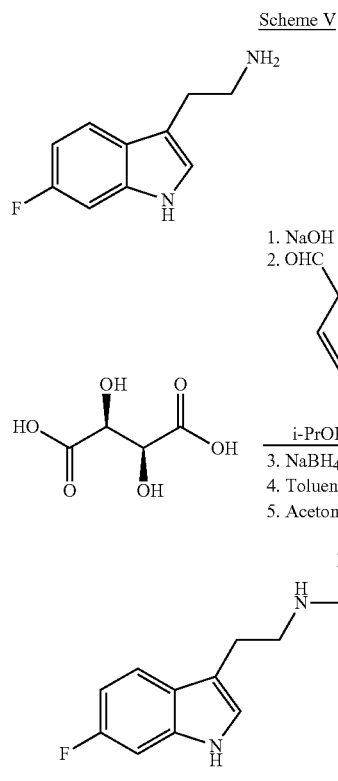

Procedure:

The tartrate salt of 2-(6-Fluoro-1H-indol-3-yl)-ethylamine (49.3 g) was stirred in a mixture of toluene (270 ml), THF (100 ml), 2M NaOH (200 ml) and 15% NaCl (65 ml). The phases were separated. The organic phase was washed with 5% NaCl (200 ml). The organic phase was concentrated under reduced pressure to dryness and the residue dissolved in isopropanol (400 ml).

3-(2,2,3,3-tetrafluoropropoxy)benzaldehyde (39 g) and isopropanol (200 ml) were charged to the reaction mixture. The reaction mixture was heated at 60° C. for 2.5 hours and then cooled to about 55° C. To the hot reaction mixture was charged a suspension of NaBH$_4$ (7.4 g) in isopropanol (100+ 50 ml). The reaction mixture was heated at 55° C. for 2.5 hours and then cooled to about 15-20° C. 2M HCl (80 ml) was added drop-wise over a period of about 30 minutes. 2M HCl (140 ml) was added over a period of 15 minutes. The mixture was stirred vigorously for 15 minutes. The mixture was concentrated to half volume followed by addition of 6M NaOH (83 ml) to pH>14. Toluene (400 ml) was added. The phases were separated and the organic phase was washed with 2M NaOH (200 ml), 3% NH$_4$Cl (200 ml) and water (200 ml), respectively. The organic phase was filtered and concentrated to dryness. The residue was dissolved in toluene (550 ml) and acetonitrile (50 ml). 6M HCl (33 ml) was added drop-wise. The resulting suspension was stirred for 2-4 hours and then filtered. The filter-cake was washed with toluene/acetonitrile (9:1, 2×75 ml) and 0.1M HCl (2×75 ml), respectively. The crude HCl salt of the compound of Formula I was dried under vacuum at about 45° C. for about 16 hours.

Final purification of HCl salt of the compound of Formula I HCl was performed by first dissolving the isolated HCl salt in acetone (300 ml). The solution was filtered and concentrated to a volume of about 90-120 ml. Filtered 0.1M HCl (1900 ml) was added drop-wise over 30 minutes. The resulting suspension was stirred at 20-25° C. for 16 hours and then filtered. The filter-cake was washed with filtered 0.1M HCl (200 ml) and filtered water (150 ml), respectively. The purified HCl salt was dried at 40° C. under vacuum for about 16 hours and isolated as a white solid. Yield: 80%. Purity by HPLC (280 nm): >99.5%. MS m/z: 399 (M+H)$^+$.

The invention claimed is:

1. A process for preparing a compound of Formula I or a salt thereof,

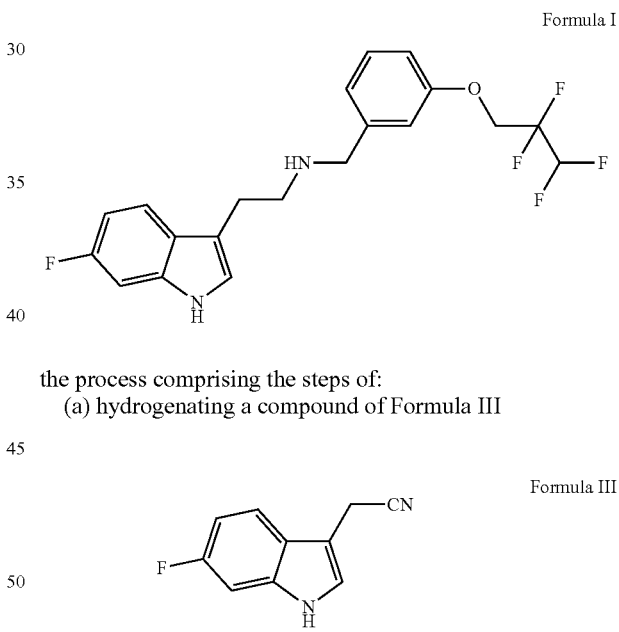

the process comprising the steps of:
(a) hydrogenating a compound of Formula III

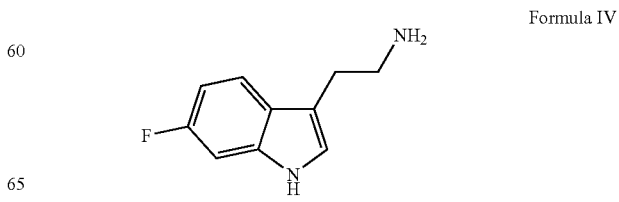

With H$_2$ in the presence of NH$_3$ and a transition metal catalyst to form the compound of Formula IV;
(b) reacting a compound of Formula IV with 3-(2,2,3,3-tetrafluoropropoxyl)-benzaldehyde in the presence of a solvent to form an imine-containing compound; and (c) reducing the imine-containing compound by using a reducing agent to form the compound of Formula I.

2. The process of claim 1, wherein the solvent in step (b) is isopropanol.

3. The process of claim 1, wherein step (b) is performed at 60° C.

4. The process of claim 1, wherein the reducing agent is sodium borohydride.

5. The process of claim 1, wherein step (c) is performed at 55° C.

6. The process of claim 1, wherein the process forms a salt of the compound of Formula I.

7. The process of claim 1, wherein the salt of the compound of Formula I is a chloride, bromide, iodide, nitrate, sulfate, phosphate, hypophosphate, metaphosphate, pyrophosphate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, a-hydroxybutyrate, butyne-1,4-dicarboxylate, hexyne-1,4-dicarboxylate, caprate, caprylate, cinnamate, citrate, formate, fumarate, glycollate, heptarioate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, or tartrate salt.

8. The process of claim 7, wherein the salt of the compound of Formula I is a chloride salt.

9. The process of claim 8, wherein the process further comprising reacting the compound of Formula I with hydrochloric acid to form the chloride salt.

10. The process of claim 1, wherein hydrogenating the compound of Formula III comprises mixing the compound of Formula III, $NH_3$ in water, and the transition metal catalyst in an alcoholic solvent to form a mixture, and hydrogenating the mixture with $H_2$.

11. The process of claim 10, wherein the transition metal catalyst is RaNi.

12. The process of claim 10, wherein the alcoholic solvent is methanol.

13. The process of claim 1, further comprising reacting a compound of Formula II

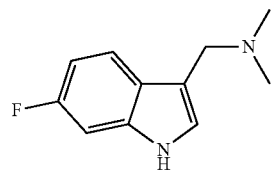

Formula II with KCN to produce the compound of Formula III.

14. The process of claim 13, wherein reacting the compound of Formula II with KCN is performed in the presence of DMF and water.

15. The process of claim 13, further comprising reacting 6-fluoroindole with formaldehyde and dimethylamine in the presence of an acidic aqueous solution to form a mixture.

16. The process of claim 15, further comprising add the mixture to a basic aqueous solution to produce the compound of Formula II.

17. The process of claim 15, wherein the formaldehyde is generated in situ from a solution of diethoxymethane, water, and formic acid.

18. The process of claim 15, wherein the acidic aqueous solution comprises acetic acid.

19. The process of claim 16, wherein the basic aqueous solution comprises sodium hydroxide.

* * * * *